US008323923B1

(12) United States Patent
Horton

(10) Patent No.: US 8,323,923 B1
(45) Date of Patent: *Dec. 4, 2012

(54) METHOD AND SYSTEM FOR PRODUCING ETHANOL

(75) Inventor: Jerry W. Horton, Rush, NY (US)

(73) Assignee: Sweetwater Energy, Inc., Rochester, NY (US)

(*) Notice: Subject to any disclaimer, the term of this patent is extended or adjusted under 35 U.S.C. 154(b) by 784 days.

This patent is subject to a terminal disclaimer.

(21) Appl. No.: 11/974,129

(22) Filed: Oct. 11, 2007

Related U.S. Application Data

(60) Provisional application No. 60/851,424, filed on Oct. 13, 2006.

(51) Int. Cl.
C12P 1/02 (2006.01)
C12P 7/06 (2006.01)
(52) U.S. Cl. .......................... 435/41; 435/161
(58) Field of Classification Search .................. 435/41, 435/161
See application file for complete search history.

(56) References Cited

U.S. PATENT DOCUMENTS

| | | | |
|---|---|---|---|
| 4,048,341 A | 9/1977 | Lagerstrom et al. | |
| 4,070,232 A | 1/1978 | Funk | |
| 4,182,780 A | 1/1980 | Lagerstrom et al. | |
| 4,201,596 A | 5/1980 | Church et al. | |
| 4,395,488 A | 7/1983 | Rowe | |
| 4,414,330 A | 11/1983 | Zucker et al. | |
| 4,447,534 A | 5/1984 | Moebus et al. | |
| 4,478,854 A | 10/1984 | Adler-nissen et al. | |
| 4,520,105 A | 5/1985 | Sinner et al. | |
| 4,600,590 A | 7/1986 | Dale | |
| 4,612,286 A | 9/1986 | Sherman et al. | |
| 4,615,742 A | 10/1986 | Wright | |
| 4,644,060 A | 2/1987 | Chou | |
| 4,806,475 A | 2/1989 | Gould | |
| 5,037,663 A | 8/1991 | Dale | |
| 5,144,008 A | 9/1992 | Ikeda et al. | |
| 5,171,592 A | 12/1992 | Holtzapple et al. | |
| 5,177,009 A | 1/1993 | Kampen | |
| 5,473,061 A | 12/1995 | Bredereck et al. | |
| 5,693,296 A | 12/1997 | Holtzapple et al. | |
| 5,726,046 A | 3/1998 | Farone et al. | |
| 5,846,787 A | 12/1998 | Ladisch et al. | |
| 5,865,898 A * | 2/1999 | Holtzapple et al. ............. 127/37 |
| 5,939,544 A | 8/1999 | Karstens et al. | |
| 5,969,189 A | 10/1999 | Holtzapple et al. | |
| 5,986,133 A | 11/1999 | Holtzapple et al. | |
| 6,043,392 A | 3/2000 | Holtzapple et al. | |
| 6,106,888 A | 8/2000 | Dale et al. | |
| 6,176,176 B1 | 1/2001 | Dale et al. | |
| 6,258,175 B1 | 7/2001 | Lightner | |
| 6,262,313 B1 | 7/2001 | Holtzapple et al. | |
| 6,365,732 B1 | 4/2002 | Van Thorre | |
| 6,416,621 B1 | 7/2002 | Karstens | |
| 6,478,965 B1 | 11/2002 | Holtzapple et al. | |
| 6,509,180 B1 | 1/2003 | Verser et al. | |
| 7,109,005 B2 | 9/2006 | Eroma et al. | |
| 7,503,981 B2 | 3/2009 | Wyman et al. | |
| 7,932,063 B2 | 4/2011 | Dunson, Jr. et al. | |
| 2002/0038058 A1 | 3/2002 | Holtzapple et al. | |
| 2002/0164730 A1 | 11/2002 | Ballesteros Perdices et al. | |
| 2002/0164731 A1 | 11/2002 | Eroma et al. | |
| 2002/0192774 A1 | 12/2002 | Ahring et al. | |
| 2002/0197686 A1 | 12/2002 | Lightner | |
| 2003/0199049 A1 | 10/2003 | Nguyen et al. | |
| 2003/0221361 A1 | 12/2003 | Russell et al. | |
| 2003/0224088 A1 | 12/2003 | Burdick | |
| 2004/0152881 A1 | 8/2004 | Holtzapple et al. | |
| 2004/0168960 A1 | 9/2004 | Holtzapple et al. | |
| 2004/0171136 A1 | 9/2004 | Holtzapple et al. | |
| 2005/0054064 A1 | 3/2005 | Talluri et al. | |
| 2005/0244934 A1 | 11/2005 | Foody et al. | |
| 2006/0003064 A1 | 1/2006 | James | |
| 2006/0024801 A1 | 2/2006 | Holtzapple et al. | |
| 2006/0069244 A1 | 3/2006 | Holtzapple et al. | |
| 2006/0188980 A1 | 8/2006 | Holtzapple et al. | |
| 2006/0251764 A1 | 11/2006 | Abbas et al. | |
| 2007/0037259 A1 | 2/2007 | Hennessey et al. | |
| 2007/0118916 A1 | 5/2007 | Puzio et al. | |

(Continued)

FOREIGN PATENT DOCUMENTS

CA 1267407 B 4/1990

(Continued)

OTHER PUBLICATIONS

Shapouri et al. 2006. The Economic Feasibility of Ethanol Production From Sugar in the United States, USDA, 78 Pages, Jul. 2006.*
Boggan. 2003. Alcohol, Chemistry and You Sources and Uses of Ethyl Alcohol. Kennesaw State University, pp. 1-5, Printed May 17, 2010. http://www.chemcases.com/alcohol/alc-03.htm/.*
N. Dowe and J. McMillan. 2001. SSF Experimental Protocols—Lignocellulosic Biomass Hydrolysis and Fermentation Laboratory Analytical Procedure (LAP), National Renewable Energy Laboratory. 1617 Cole Boulevard, Golden, Colorado. Issue Date: Oct. 30, 2001, pp. 1-18.*
Dowe et al (SSF Experimental Protocols—Lignocellulosic Biomass Hydrolysis and Fermentation. Laboratory Analytical Procedure (LAP), Issue Date: Oct. 30, 2001. National Renewable Energy Laboratory, 1617 Cole Boulevard, Golden, Colorado 80401-3393, 76 Pages).*

(Continued)

Primary Examiner — Jon P Weber
Assistant Examiner — Kailash C Srivastava
(74) Attorney, Agent, or Firm — Wilson Sonsini Goodrich & Rosati

(57) ABSTRACT

A method for producing ethanol is disclosed that uses a distributed production method where processing and pretreatment of combined liquid and solid material takes place outside of a centralized ethanol producing plant at a distributed feedstock processing plant, and separation of the resulting liquid and solid occurs prior to fermentation using this distributed production method. The resulting process liquid is then transported from each distributed feedstock processing plant to a centralized ethanol producing plant for fermentation, distillation and related processing. This novel distributed process reduces transportation costs, operating costs of ethanol producing plants, increases ethanol production throughput and improves the overall economics of ethanol production.

27 Claims, 2 Drawing Sheets

U.S. PATENT DOCUMENTS

| | | |
|---|---|---|
| 2007/0275447 A1 | 11/2007 | Lewis et al. |
| 2008/0121359 A1 | 5/2008 | Holtzapple et al. |

FOREIGN PATENT DOCUMENTS

| | | |
|---|---|---|
| EP | 1259466 B1 | 10/2008 |
| EP | 1307735 B1 | 11/2008 |
| EP | 1299170 B1 | 8/2010 |
| WO | WO 01/60752 A1 | 8/2001 |
| WO | WO 02/00324 A1 | 1/2002 |
| WO | WO 02/01220 A2 | 1/2002 |
| WO | WO 02/001220 A3 | 9/2002 |
| WO | WO 2005/118828 A1 | 12/2005 |

OTHER PUBLICATIONS

Alcohol and Tobacco Tax and Trade Bureau, treasury. 27 C.F.R. §19.134 Bonded warehouse not on premises qualified for production of spirits, p. 381, Apr. 1, 1997 revision.*

Varhegyi et al., (1989. Kinetics of the thermal decomposition of cellulose, hemicellulose, and sugarcane bagasse. Energy Fuels, vol. 3, No. 3, pp. 329-335).*

Jones et al., (1994, Ethanolic Fermentation of Blackstrap Molasses and Sugarcane Juice Using Very High Gravity Technology. J. Agric. Food Chem, vol. 42, pp. 1242-1246).*

Taylor, 2000. From raw sugar to raw materials. Chemical Innovation, vol. 30, Nos. 45-48, 1-5 Pages.*

USDA, "The Economic Feasibility of Ethanol Production From Sugar in the United States"; Jul. 2006, 69 pages.

Gum, et al. Structural characterization of a glycoprotein cellulase, 1,4-beta-D-glucan cellubiohydrolase C from Trichodermaviride. Biochem. Biophys. Acta. 1976; 446;370-86.

International search report and written opinion dated Jan. 26, 2009 for PCT/US2009/67221.

Kim, et al. Lime pretreatment and enzymatic hydrolysis of corn stover. Bioresour Technol. Dec. 2005;96(18):1994-2006.

Kim et al. Pretreatment and fractionation of corn stover by ammonia recycle percolation process. Biosour Technol. Dec. 2005;96(18):2007-13.

Lloyd, et al. Combined sugar yields for dilute sulfuric acid pretreatment of corn stover followed by enzymatic hydrolysis of the remaining solids. Bioresour Technol. Dec. 2005;96(18):1967-77.

Mosier, et al. Features of promising technologies for pretreatment of lignocellulosic biomass. Bioresour Technol. Apr. 2005;96(6):673-86.

Mosier, et al. Optimization of pH controlled liquid hot water pretreatment of corn stover. Bioresour Technol. Dec. 2005;96(18):1986-93.

Nevoigt, et al. Osmoregulation and glycerol metabolism in the yeast *Saccharomyces cerevisiae*. FEMS Microbiol. Rev. Nov. 1997;21(3):231-41.

Parekh, et al. Production of glycerol by *Hansenula anomala*. Biotechnol Bioeng. Jul. 1985;27(7):1989-91.

Taylor. From Raw Sugar to Raw materials. Chemical innovation. 2000; 30:45-48.

Waiss, et al. Improving Digestibility of Straws for Ruminant Feed by Aqueous Ammonia. Journal of Animal Science. 1972; 35(1):109-112.

Waltermann, et al. *Rhodococcus opacus* strain PD630 as a new source of high-value single-cell oil?Isolation and characterization of triacylglycerols and other storage lipids. Microbiology. 2000; 146:1143-1149.

* cited by examiner

METHOD AND SYSTEM FOR PRODUCING ETHANOL

CROSS-REFERENCES TO RELATED PATENT APPLICATIONS

This application claims the benefit of the filing date of U.S. Provisional Patent Application Ser. No. 60/851,424 entitled Method and System for Producing Ethanol, filed on Oct. 13, 2006.

BACKGROUND OF THE INVENTION

1. Field of the Invention

The invention relates generally to a method and system for producing ethanol and more particularly to a method and system for producing ethanol using one or more feedstock processing plants located near a feedstock producing or a feedstock storage site and an ethanol producing plant.

2. Description of Related Art

It is known to use a variety of different types of feedstock to produce ethanol. It is also known to utilize a number of different methods for processing feedstock into ethanol. However, each of the different conventional methods suffers from one or more disadvantages, regardless of the type of feedstock used to produce ethanol. For example, conventional methods for producing ethanol require raw, unprocessed feedstock to be transported from the site where the feedstock is produced or stored to a remote processing plant. Transportation of raw, unprocessed feedstock from the site of the feedstock producer to the ethanol producing plant results in substantial equipment, labor, fuel, maintenance and repair costs. More particularly, the transportation of raw, unprocessed feedstock results in an ethanol yield (by weight) of approximately 33% of the feedstock (by weight). In addition, the transportation of raw, unprocessed feedstock results in byproduct at the ethanol producing plant which amounts to approximately 33% (by weight) of the feedstock (by weight). Additional transportation costs, including labor, fuel, maintenance and repair, are incurred in connection with the removal of the byproducts from the ethanol producing plant. Further, conventional methods for producing ethanol require large storage capacities at either or both the site of the feedstock producer and the ethanol producing plant.

It would be desirable, therefore, if a method and system for producing ethanol could be provided that reduces the transportation costs associated with the production of ethanol from feedstock. It would also be desirable if such a method and system could be provided that would reduce the tonnage of feedstock transported from a feedstock provider to an ethanol producer. It would be further desirable if such a method and system could be provided that would produce byproducts that may be left at the site of the feedstock provider to be used as animal feed, animal bedding, compost, biofuel, chemicals, or the like. It would also be desirable if such a method and system could be provided that would produce a non-hazardous material to be transported from the feedstock provider to the ethanol producer. It would also be desirable if such a method and system could be provided that would reduce the storage requirements at an ethanol producing plant. It would be further desirable if such a method and system could be provided that would reduce or eliminate the environmental impact caused by the storage of feedstock, the disposal of byproducts, waste products and waste water, and the transportation of feedstock to an ethanol producing plant. It would be still further desirable if such a method and system could be produced that would reduce the size and cost of an ethanol producing plant and improve the efficiency of such a plant.

It is an object of the present invention to provide a method and system for producing ethanol that reduces the transportation costs associated with the production of ethanol from feedstock. It is also an object of the present invention to provide a method and system that reduces the tonnage of feedstock transported from a feedstock provider to an ethanol producer. It is another object of the present invention to provide a method and system that produces byproducts that may be left at the site of the feedstock provider to be used as animal feed, animal bedding, compost, biofuel, chemicals, or the like. It is still another object of the present invention to provide a method and system that produces a non-hazardous material to be transported from the feedstock provider to the ethanol producer. It is yet another object of the present invention to provide a method and system that reduces the storage requirements at the ethanol producing plant. It is a further object of the present invention to provide a method and system that reduces or eliminates the environmental impact caused by the storage of feedstock, the disposal of byproducts, waste products and waste water, and the transportation of feedstock to an ethanol producing plant. It is still another object of the present invention to provide a method and system that reduces the size and cost of an ethanol producing plant and improves the efficiency of such a plant.

These and other objects of the present invention will become apparent from an examination of the drawings, specification and claims contained herein.

As used, herein, the term "feedstock" shall refer to hard grains, starches, cellulose, hemicellulose and lignocellulosic biomasses such as corn stover, cereal straws, sugarcane bagasse, sawdust and paper pulp, waste materials, biomasses farmed for the sole purpose of producing ethanol such as switchgrass, old and/or poor quality animal feed, animal manure, paper, cardboard and the like. It is provided, however, that the term "feedstock" includes any material or substance that may be used to produce ethanol.

As used herein, the term "sugar water" shall refer to the substance produced by the one or more feedstock processing plants of the preferred embodiments of the present invention. More particularly, the term "sugar water" refers to the mixture of sugar and water produced by the mechanical destruction or grinding, the pretreatment, the liquefaction and the enzymolation of feedstock followed by the separation of wet animal feed. The term "sugar water" also refers to a concentrated form of the substance produced by the previously described process. It is also provided within the scope of the present invention that the term "sugar water" refers to a precursor substance of the concentrated form produced by the process described above. For example, the term "sugar water" may refer to the substance produced by the mechanical destruction or grinding of feedstock, or the term "sugar water" may refer to the substance produced by the mechanical destruction or grinding and the pretreatment of feedstock, or the term "sugar water" may refer to the substance produced by the mechanical destruction or grinding, the pretreatment and the liquefaction and the enzymolation of the feedstock. In a preferred embodiment of the present invention, the term "sugar water" refers to a non-hazardous, liquid-processed water based precursor to ethanol.

BRIEF SUMMARY OF THE INVENTION

In accordance with the present invention, there is provided a method for producing ethanol, the method comprising the steps of providing feedstock; processing the feedstock at a distributed feedstock processing plant adapted to produce sugar water and wet animal feed wherein processing comprises the steps of mechanical destruction, pretreatment, and enzymatic hydrolysis; separating the resulting sugar water and wet animal feed; transporting the sugar water from the distributed feedstock processing plant to a centralized ethanol producing plant; and producing ethanol from the transported sugar water at the centralized ethanol producing plant.

The foregoing paragraph has been provided by way of introduction, and is not intended to limit the scope of the invention as described and claimed herein.

BRIEF DESCRIPTION OF THE DRAWINGS

The various embodiments of the present invention are illustrated in the accompanying drawings, in which.

The present invention will be described in connection with a preferred embodiment, however, it will be understood that there is no intent to limit the invention to the embodiment described. On the contrary, the intent is to cover all alternatives, modifications, and equivalents as may be included within the spirit and scope of the invention as defined by this specification, drawings, and claims contained herein.

DESCRIPTION OF THE PREFERRED EMBODIMENTS

Figure 1:
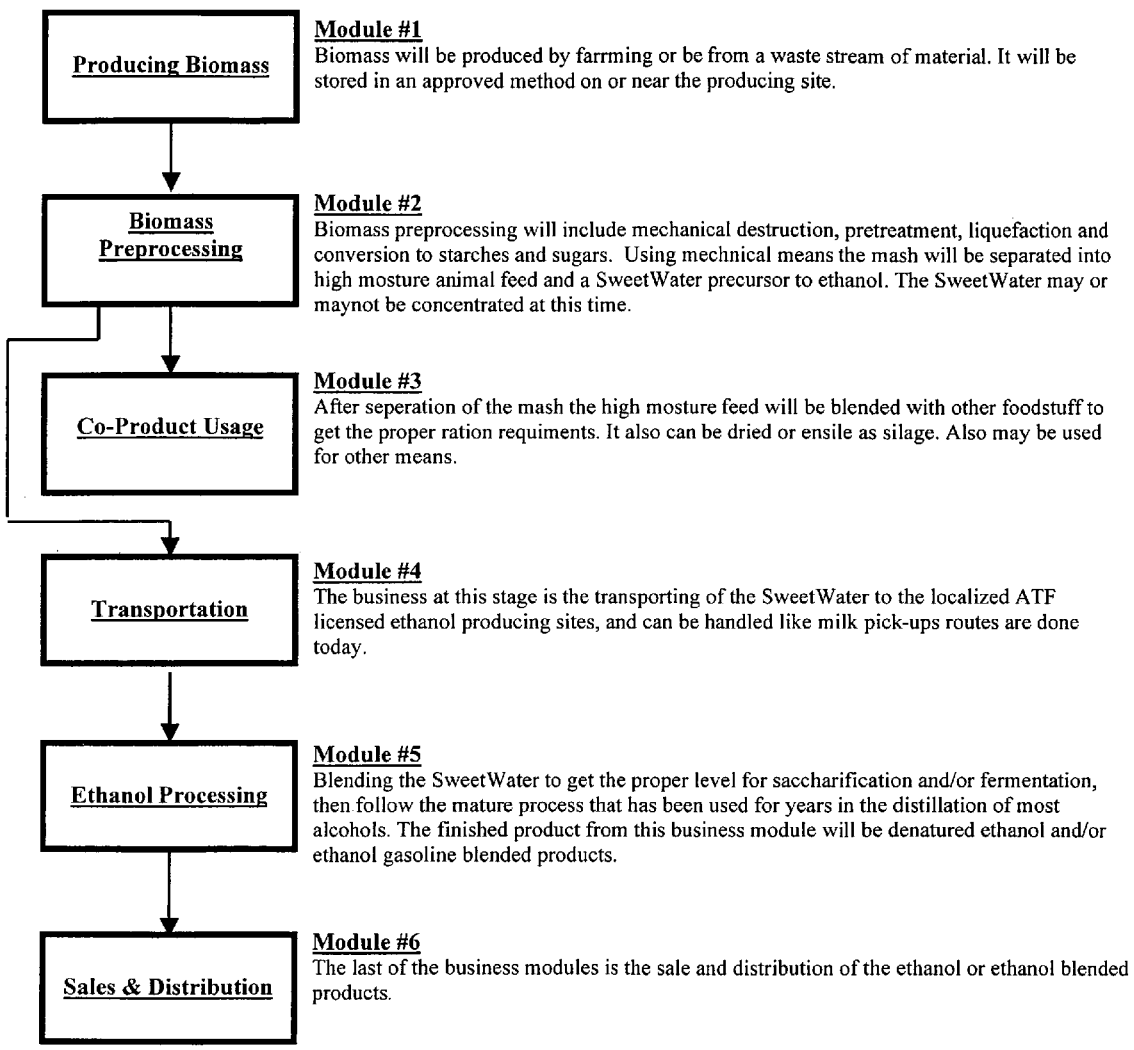
FIG. 1 is a schematic illustration of the major steps of the present invention.

For a general understanding of the present invention, reference is made to the drawings. As shown in FIG. 1, the first step of the present invention is producing biomass. Feedstock providers who produce biomass include farmers who plant, manage and harvest crops such as corn. Feedstock providers may also include feedstock storage facilities, food processors, recycle centers and the like. Feedstock providers may also include those who specifically produce feedstock for the sole purpose of producing ethanol. The feedstock provided may include hard grains, cellulose biomasses, waste materials, biomasses farmed for the sole purpose of producing ethanol, old and/or poor quality animal feed, animal manure and the like. It is provided, however, that the feedstock provided may include any material or substance that may be used to produce ethanol. While Figure depicts a preferred method and system for producing biomass, it is considered within the scope of the invention, however, that any suitable method and system for producing biomass may be used.

Still referring to FIG. 1, the second step of the preferred method and system for producing ethanol is pre processing the biomass. The preferred pre processing of biomass step is performed at a feedstock providing site. As a result, it is provided that the preferred method and system for producing ethanol will include a plurality of feedstock processing plants located at or near feedstock providing sites. The preferred feedstock processing plants are non-fermenting, non-distilling plants that do not require a license to operate from the United States Department of Alcohol Tobacco and Firearms ("ATF"). Further, the preferred feedstock processing plants produce non-hazardous materials that may be transported as such. Still further, the preferred feedstock processing plants may be portable. The portability of the preferred feedstock processing plant contributes to the transportation cost savings provided by the present invention.

Still referring to FIG. 1, the preferred processing step converts the feedstock into two products; namely, sugar water and wet animal feed. The feedstock may be processed in any number of ways including the following: (1) mechanical destruction (grinding) of the feedstock; (2) pretreatment of the feedstock; and (3) enzymolation, enzymolosis or enzymatic hydrolysis of the feedstock. The pretreatment of the feedstock may include dilute-acid thermochemical pretreatment adapted to hydrolyze the feedstock and break down the feedstock into its component sugars, e.g., xylose, etc. The pretreatment of the feedstock may also solubize a portion of the lignin. Processing of the feedstock also includes enzymatic hydrolysis in which enzymes are used to convert cellulosic biomass into fermentable sugars. More particularly, enzymatic hydroloysis is adapted to release the feedstock's sugars, e.g., glucose. The preferred pretreatment is adapted to make the cellulose of the feedstock more accessible to further treatment. In the preferred embodiment of the method and system for producing ethanol, the sugars of the pretreated feedstock are later fermented into fuel ethanol and the residue lignin may be used for catalytic conversion to other products, gasified or combusted to provide heat and power for plant operation or be offered for sale.

Still referring to FIG. 1, the biomass preprocessing step of the preferred method may also include concentrating the precursor/sugar water. The biomass preprocessing step of FIG. 1 reduces the transportation costs associated with the production of ethanol from feedstock, as described in more detail below. While FIG. 1 depicts a preferred method and system for biomass preprocessing, it is considered within the scope of the present invention that any suitable method for biomass preprocessing may be used.

Referring still to FIG. 1, the third step of the preferred method and system for producing ethanol is separating the precursor/sugar water and wet animal feed and co-product usage. As described in FIG. 1, the wet animal feed has multiple uses. In addition, the separation of the wet animal feed from the precursor/sugar water further reduces the transportation costs associated with the production of ethanol from feedstock as described in more detail below.

Still referring to FIG. 1, the fourth step of the preferred method and system for producing ethanol is transporting the sugar water from the feedstock processing plant or plants to the ethanol producing plant. In the most preferred embodiment of the method and system for producing ethanol, the tonnage that is shipped from the feedstock processing plant to the ethanol producing plant is 100% usable material. Any byproducts generated at the feedstock processing plant may be used as animal feed, animal bedding, compost, biofuel, chemicals, or they can be land applied. Further, in a preferred embodiment of the method and system for producing ethanol, the precursor/sugar water produced by the feedstock processing plant or plants is a non-hazardous material with relatively few transportation restrictions.

As noted above, steps two and three of FIG. 1 reduce transportation costs. More particularly, instead of transporting raw, non-processed feedstock from the feedstock providing site, the preferred method and system for producing ethanol requires that only processed feedstock or precursor/sugar water be transported from the feedstock providing site to the ethanol producing plant. As a result, tonnage and costs such as labor, fuel, repair and maintenance are reduced. By way of example, it is estimated that tonnage may be reduced by approximately 66% to 75% using the method of the present invention. In addition, storage capacity at the ethanol producing plant may be reduced, thereby minimizing or eliminating the adverse environmental impact caused by storage of feedstock. It is estimated that the total transportation costs associated with incoming feedstock and outgoing byproducts or waste materials may be reduced by approximately 80% using the present invention.

Still referring to FIG. 1, the fifth step of the preferred method and system for producing ethanol is processing ethanol. The finished product may be denatured ethanol or an ethanol and gasoline blend. In a preferred embodiment of the method and system for producing ethanol, ethanol is produced at an ethanol producing plant from sugar water transported from one or more feedstock processing plants. The preferred ethanol producing plant is a centrally-located (relative to a plurality of feedstock processing plants) site which receives concentrated sugar water from feedstock processing plants and blends the sugar water to the proper sugar level for fermentation. Because ethanol is a form of alcohol, a producer must be licensed by the United States Department of Alcohol Tobacco and Firearms ("ATF"). The fermentation process produces what is commonly referred to as beer. More particularly, the fermentation process yields ethanol and carbon dioxide. After completion of the fermentation step, the beer is then preferably distilled and dehydrated into 200 proof ethanol by removing the remaining amount of water in the liquid. In a preferred embodiment, the final step is called denaturing which is a process for making the liquid unfit for human consumption. The wastewater produced by the process may be used to dilute the concentrated sugar water, thereby avoiding and/or reducing treatment requirements. Because the feedstock tonnage transported to the ethanol producing plant is reduced during the feedstock processing and separating steps of the preferred method for producing ethanol, the size, land acquisition cost and plant construction cost of the ethanol producing plant will be reduced.

While FIG. 1 illustrates the preferred processes performed at the ethanol producing plant, it is considered within the scope of the invention that one or more of these processes may be performed at the one or more feedstock processing plants. In such case, it may be necessary to obtain an ATF license for each such feedstock processing plant. In the alternative, one or more of the processes performed in the first three steps of the preferred method and system for producing ethanol may be performed at the ethanol producing plant. Further, while FIG. 1 illustrates preferred processes for converting sugar water into ethanol, it is contemplated within the scope of the invention that any suitable process for converting sugar water into ethanol may be used.

Still referring to FIG. 1, the sixth step of the preferred method and system for producing ethanol is selling and distributing the ethanol or ethanol blended products produced at the ethanol producing plant. In a preferred embodiment of the present invention, the ethanol and ethanol blended products are sold and distributed to retail liquid fuel pumping locations. It is considered within the scope of the present invention that ethanol and ethanol blended products may be sold and distributed to any suitable purchaser and/or distributor. At the present time, the two most common ethanol blended products are E10 and E85. However, it is contemplated that the preferred embodiments of the method and system for producing ethanol may be used to produce many other different blends in the future. In addition, it is considered within the scope of the present invention that the preferred embodiments of the method and system for producing ethanol may also be used to produce wet cattle feed, dry cattle feed, 190 proof ethanol, 200 proof ethanol, direct injection fuel and liquid carbon dioxide.

Figure 2:
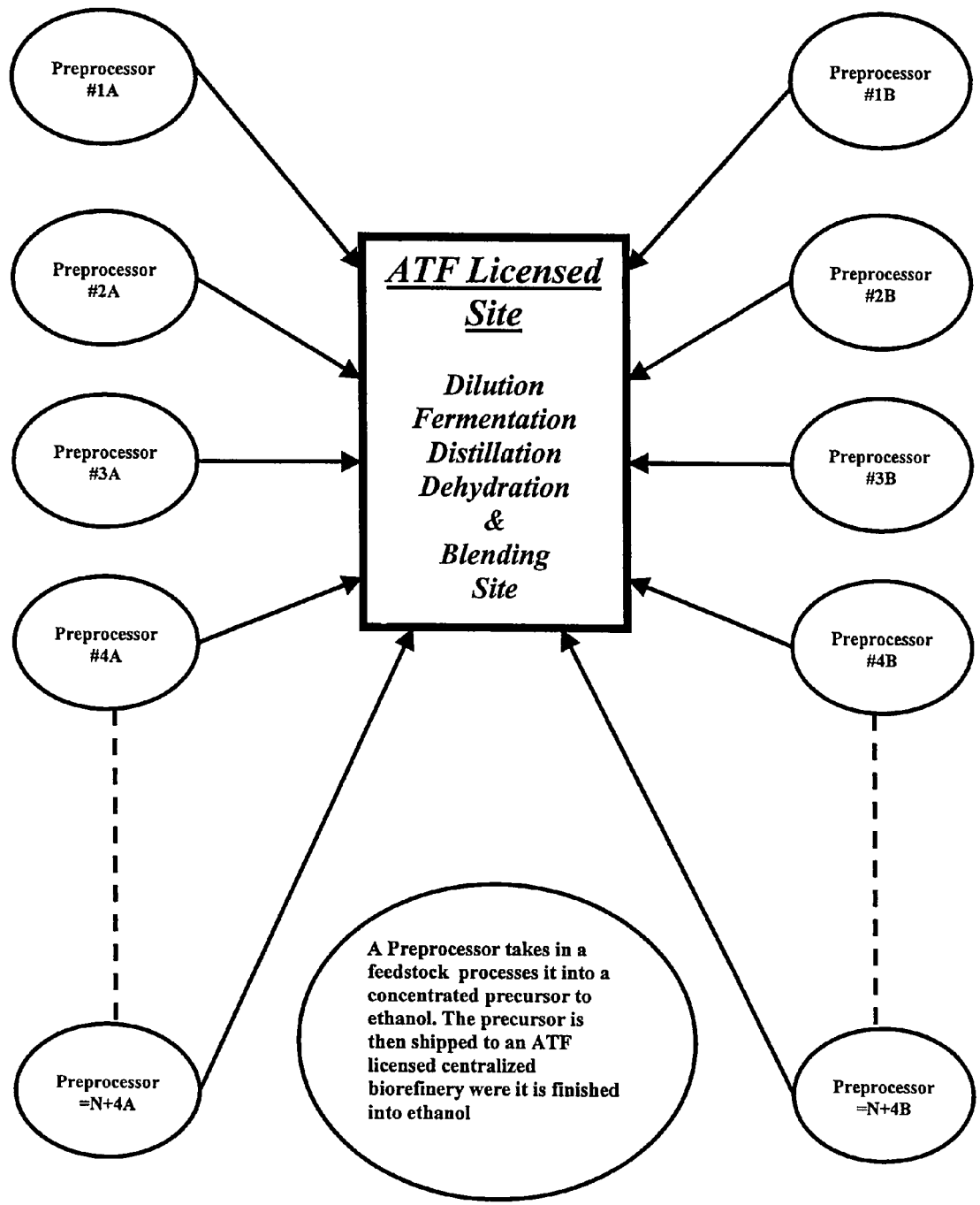
FIG. 2 is a schematic illustration of distributed processing of the present invention.

As shown in FIG. 2, the preferred method and system for producing ethanol employs a plurality of feedstock processing plants (preprocessors) and a centrally-located, ATF-licensed ethanol producing plant. According to the present invention, feedstock is processed into sugar water at a plurality of feedstock processing plants. Thereafter, the precursor/sugar water is transported to a centrally-located, ATF-licensed ethanol producing plant where it is converted into ethanol. While FIG. 2 illustrates a plurality of feedstock processing plants, it is also considered within the scope of the present invention that only one feedstock processing plant may be employed in accordance with the present invention. In addition, while FIG. 2 identifies certain processes performed at the plurality of feedstock processing plants and other processes performed at the centrally-located ethanol producing plant, it is also considered within the scope of the present invention that fewer or more processes may be performed at the plurality of feedstock processing plants and fewer or more processes may be performed at the centrally-located ethanol producing plant.

In use, several advantages of the present invention are achieved. For example, the present invention reduces transportation costs associated with the production of ethanol from feedstock. The present invention also provides a method and system that reduces the tonnage of feedstock transported from a feedstock provider to an ethanol producer. The present invention further provides a method and system that produces byproducts that may be left at the site of the feedstock provider to be used as animal feed, animal bedding, compost, biofuel, chemicals, or the like. In addition, the present invention provides a method and system that produces a nonhazardous material to be transported from the feedstock provider to the ethanol producer. The present invention also provides a method and system that reduces the storage requirements at the feedstock processor plants and the ethanol producer plant. The present invention further provides a method and system that reduces or eliminates the environmental impact caused by the storage of feedstock, the disposal, of byproducts, waste products and waste water, and the transportation of feedstock to an ethanol producing plant. The present invention still further provides a method and system that reduces the size and cost of an ethanol producing plant and improves the efficiency of such a plant.

In addition, the present invention provides a method and system that utilizes largely untapped resources as feedstock. The feedstock utilized by the preferred embodiments is more abundant, less costly to produce and contains greater potential energy than feedstock that is more commonly utilized in the production of ethanol. The present invention provides a method and system that allows feedstock providers to utilize the byproducts of the feedstock processing and derive revenue from feedstock sources that have traditionally been treated as waste.

Although this description contains many specifics, these should not be construed as limiting the scope of the present invention but as merely providing illustrations of some of the presently preferred embodiments thereof, as well as the best mode contemplated by the inventors of carrying out the invention. The invention, as described herein, is susceptible to various modifications and adaptations, and the same are intended to be comprehended within the meaning and range of equivalents of the appended claims.

What is claimed is:
1. A distributed production method for producing sugar water and ethanol, the method comprising the steps of:
   a) providing a feedstock comprising cellulose, hemicellulose, and/or lignocellulose to each of a plurality of portable feedstock processing plants each of which is located at or near a feedstock providing site;

b) processing the cellulose, hemicellulose, and/or lignocellulose of the feedstock at the plurality of portable feedstock processing plants to produce a sugar water and one or more byproducts, wherein processing comprises mechanical destruction or grinding, pretreatment, and enzymatic hydrolysis;

c) separating the sugar water produced from the cellulose, hemicellulose, and/or lignocellulose from the one or more byproducts at the plurality of portable feedstock processing plants;

d) concentrating the separated sugar water at the plurality of portable feedstock processing plants;

e) transporting the concentrated sugar water from the plurality of portable feedstock processing plants to a centralized ethanol producing plant; and f) producing ethanol from the transported sugar water at the centralized ethanol producing plant.

2. A distributed production method for producing sugar water and ethanol, the method comprising the steps of:

a) providing a feedstock comprising cellulose, hemicellulose, and/or lignocellulose to each of a plurality of portable feedstock processing plants each of which is located at or near a feedstock providing site;

b) processing the cellulose, hemicellulose, and/or lignocellulose of the feedstock at the plurality of portable feedstock processing plants to produce a sugar water and one or more byproducts, wherein processing comprises mechanical destruction or grinding, pretreatment, and enzymatic hydrolysis;

c) separating the sugar water produced from the cellulose, hemicellulose, and/or lignocellulose from the one or more byproducts at the plurality of portable feedstock processing plants;

d) transporting the concentrated sugar water from the plurality of portable feedstock processing plants to a centralized ethanol producing plant; and e) producing ethanol from the transported sugar water at the centralized ethanol producing plant.

3. A distributed production method for producing sugar water and ethanol, the method comprising the steps of:

a) providing a feedstock comprising cellulose, hemicellulose, and/or lignocellulose to each of a plurality of portable feedstock processing plants each of which is located at or near a feedstock providing site;

b) processing the cellulose, hemicellulose, and/or lignocellulose of the feedstock at the plurality of portable feedstock processing plants to produce a sugar water comprising xylose, and one or more products and/or byproducts, wherein processing comprises mechanical destruction or grinding, dilute acid thermochemical treatment, and enzymatic hydrolysis;

c) separating the sugar water comprising xylose from the one or more products and/or byproducts at the plurality of portable feedstock processing plants;

d) concentrating the separated sugar water at the plurality of portable feedstock processing plants;

e) transporting the concentrated sugar water from the plurality of portable feedstock processing plants to a centralized ethanol producing plant; and f) producing ethanol from the transported sugar water at the centralized ethanol producing plant.

4. A distributed production method for producing sugar water and ethanol, the method comprising the steps of:

a) providing a feedstock comprising cellulose, hemicellulose, and/or lignocellulose to each of a plurality of portable feedstock processing plants each of which is located at or near a feedstock providing site;

b) processing the cellulose, hemicellulose, and/or lignocellulose of the feedstock at the plurality of portable feedstock processing plants to produce a sugar water comprising glucose, and one or more products and/or byproducts, wherein processing comprises mechanical destruction or grinding, dilute acid thermochemical treatment, and enzymatic hydrolysis;

c) separating the sugar water comprising glucose from the one or more products and/or byproducts at the plurality of portable feedstock processing plants;

d) concentrating the separated sugar water at the plurality of portable feedstock processing plants;

e) transporting the concentrated sugar water from the plurality of portable feedstock processing plants to a centralized ethanol producing plant; and f) producing ethanol from the transported sugar water at the centralized ethanol producing plant.

5. The method of claim 1, wherein the producing step comprises producing ethanol from the transported sugar water at the centralized ethanol producing plant by fermenting the sugar water.

6. The method of claim 1, wherein the feedstock comprising cellulose, hemicellulose, and/or lignocellulose is corn stover, cereal straws, sugarcane bagasse, sawdust and paper pulp, waste materials, switchgrass, animal feed, animal manure, paper, cardboard, or a combination thereof.

7. The method of claim 1, wherein the one or more byproducts are used as animal feed, animal bedding, or compost.

8. The method of claim 1, wherein the pretreatment comprises dilute-acid thermochemical treatment.

9. The method of claim 1, further comprising providing the plurality of portable feedstock processing plants.

10. The method of claim 1, wherein the processing comprises hydrolysis of the cellulose, hemicellulose, and/or lignocellulose to one or more component sugars.

11. The method of claim 5, further comprising distilling the fermented sugar water to produce a distillate.

12. The method of claim 5, further comprising denaturing the ethanol.

13. The method of claim 5, further comprising selling the ethanol produced at the ethanol producing plant.

14. The method of claim 10, wherein the one or more component sugars comprise xylose.

15. The method of claim 10, wherein the one or more component sugars comprise glucose.

16. The method of claim 11, further comprising dehydrating the distillate.

17. The method of claim 2, wherein the producing step comprises producing ethanol from the transported sugar water at the centralized ethanol producing plant by fermenting the sugar water.

18. The method of claim 2, wherein the feedstock comprising cellulose, hemicellulose, and/or lignocellulose is corn stover, cereal straws, sugarcane bagasse, sawdust and paper pulp, waste materials, switchgrass, animal feed, animal manure, paper, cardboard, or a combination thereof.

19. The method of claim 2, wherein the one or more byproducts are used as animal feed, animal bedding, or compost.

20. The method of claim 2, wherein the pretreatment comprises dilute-acid thermochemical treatment.

21. The method of claim 2, wherein the processing comprises hydrolysis of the cellulose, hemicellulose, and/or lignocellulose to one or more component sugars.

22. The method of claim 17, further comprising distilling the fermented sugar water to produce a distillate.

23. The method of claim 17, further comprising denaturing the ethanol.

24. The method of claim 17, further comprising selling the ethanol produced at the ethanol producing plant.

25. The method of claim 21, wherein the one or more component sugars comprise xylose.

26. The method of claim 21, wherein the one or more component sugars comprise glucose.

27. The method of claim 22, further comprising dehydrating the distillate.

* * * * *